(12) United States Patent
Jia et al.

(10) Patent No.: US 10,993,901 B2
(45) Date of Patent: May 4, 2021

(54) COMPOSITION FOR WASHING AND CONDITIONING THE HAIR

(71) Applicant: L'OREAL, Paris (FR)

(72) Inventors: Haidong Jia, Shanghai (CN); Yixi Zhou, Shanghai (CN); Chensu Xu, Shanghai (CN)

(73) Assignee: L'OREAL, Paris (FR)

( * ) Notice: Subject to any disclaimer, the term of this patent is extended or adjusted under 35 U.S.C. 154(b) by 702 days.

(21) Appl. No.: 15/531,025

(22) PCT Filed: Dec. 25, 2014

(86) PCT No.: PCT/CN2014/094927
§ 371 (c)(1),
(2) Date: May 26, 2017

(87) PCT Pub. No.: WO2016/101207
PCT Pub. Date: Jun. 30, 2016

(65) Prior Publication Data
US 2017/0333332 A1    Nov. 23, 2017

(51) Int. Cl.
| | | |
|---|---|---|
| A61Q 5/02 | (2006.01) | |
| A61Q 5/12 | (2006.01) | |
| A61K 8/81 | (2006.01) | |
| A61K 8/37 | (2006.01) | |
| A61K 8/60 | (2006.01) | |
| A61K 8/41 | (2006.01) | |
| A61K 8/73 | (2006.01) | |
| A61K 8/31 | (2006.01) | |
| A61K 8/44 | (2006.01) | |
| A61K 8/46 | (2006.01) | |

(52) U.S. Cl.
CPC .............. *A61K 8/8158* (2013.01); *A61K 8/31* (2013.01); *A61K 8/375* (2013.01); *A61K 8/416* (2013.01); *A61K 8/442* (2013.01); *A61K 8/463* (2013.01); *A61K 8/602* (2013.01); *A61K 8/604* (2013.01); *A61K 8/731* (2013.01); *A61K 8/737* (2013.01); *A61K 8/817* (2013.01); *A61Q 5/02* (2013.01); *A61Q 5/12* (2013.01); *A61K 2800/262* (2013.01); *A61K 2800/34* (2013.01)

(58) Field of Classification Search
None
See application file for complete search history.

(56) References Cited

U.S. PATENT DOCUMENTS

| | | | |
|---|---|---|---|
| 2004/0247630 A1 | 12/2004 | Seipel et al. | |
| 2006/0039956 A1 | 2/2006 | Hensen et al. | |
| 2006/0135382 A1* | 6/2006 | Molenda | A61K 8/37 510/119 |
| 2006/0135393 A1 | 6/2006 | Molenda | |
| 2010/0249004 A1 | 9/2010 | Fack | |
| 2011/0142778 A1* | 6/2011 | Hloucha | A61K 8/068 424/70.13 |
| 2014/0023606 A1 | 1/2014 | Scheunemann et al. | |
| 2017/0000706 A1* | 1/2017 | Bobbert | A01N 25/30 |

FOREIGN PATENT DOCUMENTS

| | | |
|---|---|---|
| DE | 10306838 A1 | 8/2004 |
| EP | 1932512 A1 | 6/2008 |
| EP | 2 198 850 A1 | 6/2010 |
| JP | 2010-106032 A | 5/2010 |
| JP | 2014-509610 A | 4/2014 |

OTHER PUBLICATIONS

Certified Organic Cosmetics "Dicapryl Ether " (2013).*
Office Action dated Feb. 18, 2019 in corresponding Japanese Patent Application No. 2017-528805 (with English Translation), 14 pages.
Schwarzkoph & Henkel, Germany, "Restorative Shampoo", Mintel GNPD, Nov. 2014, ID#2807371, (English Translation Previously Filed ), 2 pages, URL, http://www.portal.mintel.com.
Coop, Switzerland, "Shampoo", Mintel GNPD, May 2014, ID#2430517, (English Translation Previously Filed ), 2 pages URL, http://www.portal.mintel.com.
L'Occitane, France, "Shampoo", Mintel GNPD, Oct. 2014, ID#2710903, (English Translation Previously Filed ), 2 pages URL, http://www.portal.mintel.com.
L'Occitane, France, "Shampoo", Mintel GNPD, Jun. 2014. ID#2482361, (English Translation Previously Filed ), 2 pages URL, http://www.portal.mintel.com.
Apivita, Greece, "Volumising Shampoo for Fine and Toneless Hair", Mintel GNPD, May 2010, ID#1320492, (English Translation Previously Filed ), 2 pages, URL, http://www.portal.mintel.com.
Extended European Search Report dated Jun. 15. 2018 in Patent Application No. 14908775.1, 10 pages.
"Restorative Shampoo" Database GNPD [Online], Mintel, XP002781443, Nov. 2014, 3 Pages.
"Shampoo" Database GNPD [Online], Mintel, XP002781444, May 2014, 3 Pages.
"Shampoo" Database GNPD [Online], Mintel, XP002781445, Oct. 2014, 3 Pages.
"Shampoo" Database GNPD [Online], Mintel, XP002781446, Jun. 2014, 3 Pages.
"Volumising Shampoo for Fine and Toneless Hair" Database GNPD [Online], Mintel, XP002781447, May 2010, 3 Pages.
International Search Report and Written Opinion dated Jul. 24, 2015, in PCT/CN2014/094927, filed Dec. 25, 2014.

* cited by examiner

*Primary Examiner* — Jyothsna A Venkat
(74) *Attorney, Agent, or Firm* — Oblon, McClelland, Maier & Neustadt, L.L.P.

(57) ABSTRACT

Provided is a composition comprising, in an aqueous phase at least one anionic surfactant, at least one amphoteric and/or zwitterionic surfactant, at least one alkyl(poly)glycoside nonionic surfactant, at least on polymer chosen from cationic polymers of cationic cellulose, cationic alkyldiallylamine or dialkyldiallylammonium cyclopolymer, amphoteric polymers which comprising one or more units derived from a monomer of (meth)acrylate or (meth)acrylamide type, a monomer of (meth)acrylamidoalkyltrialkylammonium type, or a monomer of (meth)acrylic type, or a mixture thereof, and at least on fatty acid ester of glycerol and/or of polyglycerol.

3 Claims, No Drawings

COMPOSITION FOR WASHING AND CONDITIONING THE HAIR

FIELD OF THE INVENTION

The present invention relates to hair care cosmetic field, more specifically, it relates to new compositions having improved conditioning properties to the hair after application.

BACKGROUND OF THE INVENTION

It is known to the art to use detergent and conditioning hair care composition, or shampoos, based essentially on surfactants, in particular of the anionic, nonionic, and/or amphoteric type, in combination with conditioning agents.

Surfactants such as anionic surfactants, amphoteric surfactants, or a mixture are commonly known for the ability of removing the various kinds of soil initially present in the hair, and thus possess good washing power. However along with this property, the surfactants may bring to the hair damages due to their aggressive nature of such a cleansing treatment, which leading to the pronounced damage to the hair, such as progressive removal of the lipids or proteins contained in or at the surfactant of the hair.

In order to improve the cosmetic properties of the above detergent composition, and more especially detergent compositions for application to sensitized hair, i.e., hair which is damaged or weakened, in particular through the chemical action of environmental agents and/or of hair treatments such as permanent-waving, dyeing or bleaching, it is known to introduce into these compositions conditioning agents. The main purpose of these conditioning agents is to rectify or limit the undesirable effects induced by the various treatments or types of attach to which the hair fibers are more or less repeatedly subjected to and, of course, they can also improve the cosmetic behavior of natural hair.

The conditioning agents most commonly used to date in shampoos are cationic polymers, silicones and/or silicone derivatives which impart to washed, dry or wet hair a disentangling, softness and a smoothness which are markedly enhanced in comparison to what can be obtained with corresponding cleansing compositions which do not contain them.

Moreover, it is also known to combine more than one conditioning agents in shampoos to obtain even better conditioning effect to the hair, especially to the sensitized hair. Different types of silicones and its derivatives, natural or synthetized oils are most commonly combined to achieve this purpose.

More particularly, it is known to use compositions for hair, containing surfactants such as cationic and amphoteric surfactants, coco-glucoside, glycerol oleate, and a type of guar gum. The composition as such is used in anti-hair loss and hair nourishing shampoos.

However, the conditioning effect of the compositions as mentioned above is not satisfying, especially for reducing the force during dry combing, and especially on natural hair. Moreover, the guar gum may make the composition not transparent.

There is thus a need for new products displaying improved performance in respect to the cosmetic properties mentioned above.

More particularly, there is a need for a new product which possesses a pleasant transparent or translucent appearance.

The present invention is directed towards meeting this need.

BRIEF DESCRIPTION OF THE INVENTION

One aim of the present invention is to obtain a composition, especially for washing and conditioning keratin fibers, especially the hair, and more particularly the natural hair, which possesses an improved reduction of the force during dry combing.

Moreover, the aim of the present invention is to obtain a composition for washing and conditioning keratin fibers, especially the hair, more particularly the natural hair, which is transparent or translucent.

The aim of the present invention is achieved by a composition comprising, in an aqueous phase: at least one anionic surfactant, at least one amphoteric surfactant, at least one alkyl(poly)glycoside nonionic surfactant, at least one specific polymer, and at least one fatty acid esters of glycerol and of polyglycerol.

Preferably, the composition of the present invention is transparent.

Preferably, the composition of the present invention is silicone-free.

For the purpose of the invention, the term "natural hair" refers to the hair which is not damaged or weakened, in particular through the chemical action hair treatments.

As used herein, the term "silicone-free" means the composition of the present invention comprising no silicone or comprising silicone in an amount no more than 1% by weight of silicones relative to the total composition. Preferably, the composition may contain no more than 0.5% by weight, more preferably no more than 0.2% by weight, of silicones relative to the total weight of the composition.

More preferably, the composition of the present invention does not contain silicone.

Preferably the composition is transparent or translucent.

The term "transparent or translucent" is understood to mean a composition having a turbidity of less than 400 NTU (Nephelometric Turbidity Units) at 25° C. and preferably of less than 250 NTU at 25° C., measured with a 2100N Turbidimeter machine from HACH, wherein the sample cells for turbidity testing are made of quartz glass with reference Cat. 2084900.

Preferably, the "keratin fiber" according to the present invention is the hair.

Another aspect of the invention is a process for washing and conditioning keratin fibers, especially the hair, comprising the steps of applying to said fibers the composition of the invention, and then rinsing with water after an optional period of exposure.

Yet another aspect of the present invention is the use of the above composition of the invention for washing and/or conditioning keratin fibers, especially hair.

In the description, the terms "at least a" or "at least one" are equivalent to "one or more".

Other characteristics and advantages of the invention will emerge more clearly on reading the description and the examples that follow.

DETAILED DESCRIPTION OF THE PRESENT INVENTION

Surfactants

The composition according to the invention comprises, as surfactants (also called surface active agent), at least one anionic surfactant and at least one amphoteric surfactant.

i) Anionic Surfactants

The composition of the invention comprises at least one anionic surfactant or "surface-active agent".

Anionic surfactant is understood to mean an amphiphilic compound with a hydrophobic part and a hydrophilic part wherein the hydrophilic part carries as ionic or ionisable group only anionic group with a cationic counterion which is generally metallic (alkali metal, such as Na or K) or ammonium, capable of dissociating to give anions in aqueous solution.

More particularly the anionic group of the anionic surfactant is belonging to the group chosen from: $C(O)OH$, $-C(O)O^-$, $-SO_3H$, $-S(O)_2O^-$, $-OS(O)_2OH$, $-OS(O)_2O^-$, $-P(O)OH_2$, $-P(O)_2O^-$, $-P(O)O_2^-$, $-P(OH)_2$, $=P(O)OH$, $-P(OH)O^-$, $=P(O)O^-$, $=POH$, $=PO^-$, the cationic counter anion being usually selected from alkali metal such as sodium, or alkaline earth metal such as magnesium, or organic cationic counter anion such as ammonium salts, amine salts, or aminoalcohol salts. The surfactants may also occur in their acid forms.

Mention may be made, as anionic surfactants, of surfactants comprising carboxylate, sulfate, sulfonate, sulfoacetate, sulfosuccinate, phosphate, isethionate, sarcosinate, glutamate, lactylate or taurate anionic groups, salts of fatty acids, salts of galactosiduronic acids, salts of ether carboxylic acids surfactants and their mixtures.

More particularly, the anionic surfactants according to the invention are chosen from:

$(C_6-C_{30})$alkyl sulfates, $(C_6-C_{30})$alkyl ether sulfates, $(C_6-C_{30})$alkylamido ether sulfates, alkylaryl polyether sulfates or monoglyceride sulfates; preferably for this type of anionic surfactants, $(C_6-C_{30})$alkyl ether sulfates, alkylaryl polyether sulfates, or a mixture is used. Mentions may be made of sulfate of ether of lauryl alcohol and alkylene oxide, containing from 1 to 50 alkylene oxide groups.

More preferably, the anionic surfactants is chosen from sulfate of ether of lauryl alcohol and alkylene oxide containing from 1 to 4 alkylene oxide groups, especially ethylene oxide groups. For example, sodium laureth sulfate containing in average 2.2 ethylene oxide groups that are sold by the company Cognis (BASF) under the name Texapon® AOS 225 UP, Rhodia under the name Rhodapex® esb-70/fla3, and Clariant under the name Genapol® LRO L'O, and sodium laureth sulfate containing in average 1 ethylene oxide group that is sold by the company Zhejiang Zanyu Technology under the name SLES (N1EO).

$(C_6-C_{30})$alkyl sulfonates, $(C_6-C_{30})$alkylamidesulfonates, $(C_6-C_{30})$alkylaryl sulfonates, α-olefin sulfonates, paraffin sulfonates;

$(C_6-C_{30})$alkyl phosphates;

$(C_6-C_{30})$alkyl sulfosuccinates, $(C_6-C_{30})$alkyl ether sulfosuccinates or $(C_6-C_{30})$alkylamido sulfosuccinates;

$(C_6-C_{30})$alkyl sulfoacetates;

$(C_6-C_{24})$acylsarcosinates;

$(C_6-C_{24})$acylglutamates;

$(C_6-C_{30})$alkylpolyglycoside carboxylic ethers;

$(C_6-C_{30})$alkylpolyglycoside sulfosuccinates;

$(C_6-C_{30})$alkyl sulfosuccinamates;

$(C_6-C_{24})$acyl isethionates, for example sodium lauroyl methyl isethionate, sodium cocoyl isthionate; mentiones may be made of the sodium lauroyl methyl isethionate which is sold under the trade name ISE-LUX® LQ-CLR-SB by the company Innospec Active Chemicals;

N—[$(C_6-C_{24})$acyl] taurates;

salts of fatty acids;

$(C_8-C_{20})$acyl lactylates;

salts of $(C_6-C_{30})$alkyl-D-galactosiduronic acids;

salts of $(C_6-C_{30})$alkyl polyoxyalkylenated ether carboxylic acids, of $(C_6-C_{30})$alkylaryl polyoxyalkylenated ether carboxylic acids or of $(C_6-C_{30})$alkylamido polyoxyalkylenated ether carboxylic acids;

and their mixtures.

The alkyl or acyl radicals of these various anionic surfactants preferably comprise from 12 to 20 carbon atoms.

Furthermore, the oxyalkylenated or polyoxyalkylenated anionic surfactants preferably comprise from 1 to 50 alkylene oxide groups, more preferably from 1 to 4 alkylene oxide groups, in particular ethylene oxide groups.

Advantageously, according to an embodiment, the present invention comprises at least one anionic surfactant chosen from $(C_6-C_{30})$alkyl sulfates, $(C_6-C_{30})$alkyl ether sulfates, $(C_6-C_{30})$alkylamido ether sulfates, alkylaryl polyether sulfates, monoglyceride sulfates, $(C_6-C_{24})$acyl isethionates, or a mixture thereof.

According to an embodiment of the present invention, the anionic surfactant is preferably chosen from sodium laureth sulfate, sodium lauroyl methyl isethionate, sodium cocoyl isethionate, or a mixture thereof.

More preferably the anionic surfactant is sodium laureth sulfate containing in average 2.2 ethylene oxide groups.

Advantageously, the content of anionic surfactant(s) represents from 0.1% to 50% by weight, preferably from 1% to 40% by weight, more preferably from 5% to 25% by weight, with respect to the weight of the composition.

ii) Amphoteric or Zwitterionic Surfactants

According to an embodiment of the invention the at least one surfactant is chosen from the amphoteric or zwitterionic surfactants.

The amphoteric or zwitterionic surfactant(s) that may be used in the present invention may be quaternized secondary or tertiary aliphatic amine derivatives containing at least one anionic group, for instance a carboxylate, sulfonate, sulfate, phosphate or phosphonate group, and in which the aliphatic group or at least one of the aliphatic groups is a linear or branched chain comprising from 8 to 22 carbon atoms.

Mention may be made in particular of $(C_8-C_{20})$alkylbetaines, sulfobetaines, $(C_8-C_{20}$ alkyl)amido$(C_2-C_8$ alkyl)betaines and $(C_8-C_{20}$ alkyl)amido$(C_2-C_8$ alkyl)sulfobetaines.

Among the $(C_8-C_{20})$alkylbetaines, mentions may be made of behenylbetaine, cetyl betaine, cocoylbetaine, decylbetaine. From alkylbetaines, cocoylbetaine is preferred, for example the products sold by the company Rhodia under the tradename Mirataine® BB/FLA.

Among the optionally quaternized secondary or tertiary aliphatic amine derivatives that may be used, mention may also be made of the products of respective structures (A1) and (A2) below:

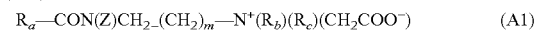

(A1)

in which:

$R_a$ represents a $C_{10}-C_{30}$ alkyl or alkenyl group derived from an acid $R_a$—COOH preferably present in hydrolysed coconut oil, a heptyl group, a nonyl group or an undecyl group, $R_b$ represents a 1-hydroxyethyl group, $R_c$ represents a carboxymethyl group;

m is equal to 0, 1 or 2,

Z represents a hydrogen atom or a hydroxyethyl or carboxymethyl group;

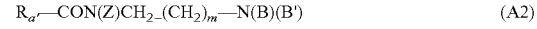

(A2)

in which:

B represents —CH$_2$CH$_2$OX', with X' representing —CH$_2$—COOH, CH$_2$—COOZ', —CH$_2$CH$_2$—COOH, —CH$_2$CH$_2$—COOZ', or a hydrogen atom, B' represents —(CH$_2$)$_z$—Y', with z=1 or 2, and Y' representing —COOH, —COOZ', —CH$_2$—CHOH—SO$_3$H or —CH$_2$—CHOH—SO$_3$Z', m' is equal to 0, 1 or 2, Z represents a hydrogen atom or a hydroxyethyl or carboxymethyl group, Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane, R$_a$' represents a C$_{10}$-C$_{30}$ alkyl or alkenyl group of an acid R$_a$COOH preferably present in hydrolysed linseed oil or coconut oil, an alkyl group, in particular a C$_{17}$ alkyl group, and its iso form, or an unsaturated C$_{17}$ group.

The compounds corresponding to formula (A1) are preferred.

Among the compounds corresponding to formula (A1), mentions may be made of cocamidopropyl betaine, for example the product sold under the tradename Dehyton PK 45 by Cognis (BASF).

Use may also be made of the compounds of formula (A3):

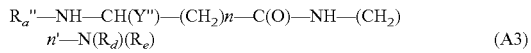

in which:

R$_a$" represents a C$_{10}$-C$_{30}$ alkyl or alkenyl group of an acid R$_a$"—C(O)OH preferably present in hydrolysed linseed oil or coconut oil;

Y" represents the group —C(O)OH, —C(O)OZ", —CH$_2$—CH(OH)—SO$_3$H or the group —CH$_2$—CH(OH)—SO$_3$—Z", with Z" representing a cationic counterion resulting from an alkali metal or alkaline-earth metal, such as sodium, an ammonium ion or an ion resulting from an organic amine;

R$_d$ and R$_e$ represent, independently of each other, a C$_1$-C$_4$ alkyl or hydroxyalkyl radical; and n and n' denote, independently of each other, an integer ranging from 1 to 3.

Among the compounds corresponding to formula (A3), mention may in particular be made of the compound classified in the CTFA dictionary under the name sodium diethylaminopropyl cocoaspartamide, such as the one sold by the company Chimex under the name Chimexane HB.

Preferably, the amphoteric surfactants are chosen from (C$_8$-C$_{20}$)alkylbetaines, (C$_8$-C$_{20}$)alkylamido(C$_1$-C$_6$)alkylbetaines, and mixtures thereof.

More preferably, the amphoteric or zwitterionic surfactant is chosen from cocamidopropyl betaine, cocoylbetaine, or a mixture thereof.

According to a preferred embodiment, the amphoteric or zwitterionic surfactant(s) is present in an amount ranging from 1% to 70% by weight, preferably from 3% to 50% by weight, more preferably from 5% to 15% by weight, relative to the total weight of the composition.

iii) Alkyl(Poly)Glycoside Nonionic Surfactants

The term "alkyl(poly)glycoside" denotes an alkylpolyglycoside or an alkylmonoglycoside, also referred to in the present patent application as an alkylglycoside, which may be alkoxylated with one or more alkylene oxide groups, preferentially of C$_2$-C$_4$.

The alkyl(poly)glycoside nonionic surfactant(s) used, alone or as mixtures, in accordance with the present invention may be represented by formula (IV) below:

in which:

R$_1$ represents a linear or branched, saturated or unsaturated alkyl group, containing from about 8 to 24 carbon atoms, or an alkyl phenyl group in which the linear or branched alkyl radical contains from 8 to 24 carbon atoms, R$_2$ represents an alkylene group containing from about 2 to 4 carbon atoms, G represents a saccharide unit containing 5 or 6 carbon atoms, t denotes a value ranging from 0 to 10 and preferably from 0 to 4, and v denotes a value ranging from 1 to 15.

Preferably, the alkyl(poly)glycoside nonionic surfactant(s) correspond to formula (IV) in which:

R$_1$ denotes a linear or branched, saturated or unsaturated alkyl group containing from 8 to 18 carbon atoms, G denotes glucose, fructose or galactose, preferably glucose, t denotes a value ranging from 0 to 3, and is preferably equal to 0, and R$_2$ and v are as defined previously.

The degree of polymerization of the alkyl(poly)glycoside nonionic surfactant(s) as represented, for example, by the index v in formula (IV) ranges on average from 1 to 15 and preferably from 1 to 4. This degree of polymerization more particularly ranges from 1 to 2 and better still from 1.1 to 1.5, on average.

The glycoside bonds between the saccharide units are 1,6- or 1,4-bonds; preferably 1,4-bonds.

The compounds of formula (IV) that may be used in the present invention are especially represented by the products sold by the company Cognis under the names Plantaren® (600 CS/U, 1200 and 2000) or Plantacare® (818, 1200 and 2000). It is also possible to use the products sold by the company SEPPIC under the names Triton CG 110 (or Oramix CG 110) and Triton CG 312 (or Oramix® NS 10), the products sold by the company BASF under the name Lutensol GD 70, or those sold by the company Chem Y under the name AG10 LK.

It is also possible, for example, to use the 1,4-(C$_8$-C$_{16}$) alkylpolyglucoside as an aqueous solution at 53% by weight relative to the total weight of the solution, sold by Cognis under the reference Plantacare® 818 UP.

Among all these alkyl(poly)glycoside nonionic surfactants, the decyl glucoside (INCI: Decyl glucoside) sold by Cognis under the reference Plantacare® 2000 UP is preferably used.

The nonionic surfactant(s) are present in amounts preferably ranging from 0.01% to 20% by weight, preferably from 0.05% to 10%, more preferably from 0.1% to 3%, relative to the total weight of the composition.

Polymers

The composition of the present invention comprises at least one polymer, chosen from cationic cellulose, cationic alkyldiallylamine or dialkyldiallylammonium cyclopolymer, amphoteric polymers which comprising one or more units derived from a monomer of (meth)acrylate or (meth)

acrylamide type, a monomer of (meth)acrylamidoalkyltrialkylammonium type, or a monomer of (meth)acrylic type, or a mixture thereof.

It is first recalled that, for the purposes of the present invention, the term "cationic polymer" denotes any polymer containing cationic groups and/or groups that can be ionized into cationic groups.

Cationic Cellulose

The cationic celluloses may be made more particularly chosen from cellulose ether derivatives comprising quaternary ammonium groups, cationic cellulose copolymers or cellulose derivatives grafted with a water-soluble quaternary ammonium monomer, or a mixture thereof.

The cellulose ether derivatives comprising quaternary ammonium groups are especially described in French patent 1 492 597, and mention may be made of the polymers (INCI name polyquaternium-10) sold under the name Ucare Polymer "JR" (JR 400 LT, JR 125 and JR 30M) or "LR" (LR 400 or LR 30M) by the company Amerchol. These polymers are also defined in the CTFA dictionary as quaternary ammoniums of hydroxyethylcellulose that have reacted with an epoxide substituted with a trimethylammonium group.

Cationic cellulose copolymers or cellulose derivatives grafted with a water-soluble quaternary ammonium monomer are described especially in U.S. Pat. No. 4,131,576, and mention may be made of hydroxyalkylcelluloses, for instance hydroxymethyl-, hydroxyethyl- or hydroxypropyl-celluloses grafted, in particular, with a methacryloylethyltrimethylammonium, methacrylamidopropyltrimethylammonium or dimethyldiallylammonium salt. The commercial products corresponding to this definition are more particularly the products sold under the names Celquat L 200 and Celquat H 100 by the company National Starch.

Preferably, the cationic cellulose of the present invention is chosen from cellulose ether derivatives, more particularly comprising quaternary ammonium groups.

Cationic Alkyldiallylamine or Dialkyldiallylammonium Cyclopolymer

The said cationic cyclopolymer may be a homopolymer or copolymer containing, as main constituent of the chain, units corresponding to formula (IV) or (V):

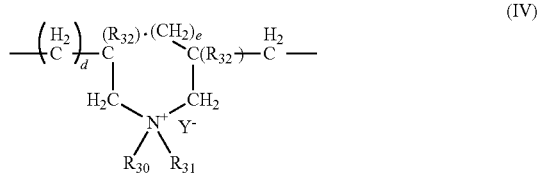

(IV)

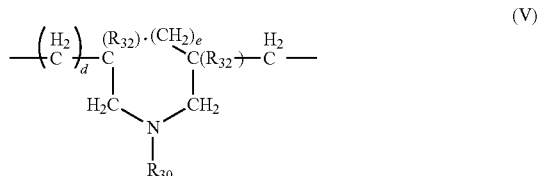

(V)

in which formula d and e are equal to 0 or 1, the sum d+e being equal to 1; $R_{32}$ denotes a hydrogen atom or a methyl radical; $R_{30}$ and $R_{31}$, independently of each other, denote a $C_1$-$C_8$ alkyl group, a hydroxyalkyl group in which the alkyl group is $C_1$-$C_5$, an amidoalkyl group in which the alkyl is $C_1$-$C_4$; $R_{30}$ and $R_{31}$ can also denote, together with the nitrogen atom to which they are attached, a heterocyclic group such as piperidyl or morpholinyl; $R_{30}$ and $R_{31}$, independently of each other, preferably denote a $C_1$-$C_4$ alkyl group; $Y^-$ is an organic or mineral anion such as bromide, chloride, acetate, borate, citrate, tartrate, bisulfate, bisulfite, sulfate or phosphate. These polymers are described in particular in FR 2 080 759 and FR 2 190 406.

Among the polymers defined above, mention may be made more particularly of the dimethyldiallylammonium chloride homopolymer sold under the name "Merquat® 100" (INCI name polyquaternium 6) by the company Nalco (and its homologues of low weight-average molecular mass) and the copolymers of diallyldimethylammonium chloride and of acrylamide, sold under the name Merquat® 550.

Amphoteric Polymer

It is also possible to use amphoteric polymers, which may preferably be chosen from amphoteric polymers comprising a repetition of:

(i) one or more units derived from a monomer of (meth)acrylate or (meth)acrylamide type, (ii) one or more units derived from a monomer of (meth)acrylamidoalkyltrialkylammonium type, and (iii) one or more units derived from an acidic monomer of (meth)acrylic acid type.

Preferably, the units derived from a monomer of (meth)acrylamide type (i) are units of structure (Ia) below:

(Ia)

in which $R_1$ denotes H or $CH_3$ and $R_2$ is chosen from an H, —O—$(CH_2)_p$ radical with p being an integer preferably from 1 to 4, and more preferably 1 or 2, amino, dimethylamino, tert-butylamino, dodecylamino or —NH—$CH_2OH$ radical.

Preferably, the said amphoteric polymer comprises a repetition of only one unit of formula (Ia).

The unit derived from a monomer of (meth)acrylate or (meth)acrylamide type of formula (Ia) in which $R_1$ denotes H and $R_2$ is —O—$CH_2$ is particularly preferred. It corresponds to the monomer per se.

Preferably, the units derived from a monomer of (meth)acrylamidoalkyltrialkylammonium type (ii) are units of structure (IIa) below:

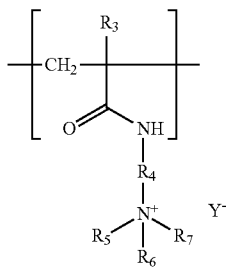

in which:
R$_3$ denotes H or CH$_3$,
R$_4$ denotes a group (CH$_2$)$_k$ with k being an integer ranging from 1 to 6 and preferably from 2 to 4, even more preferably 3;
R$_5$, R$_6$ and R$_7$, which may be identical or different, denote an alkyl group containing from 1 to 4 carbon atoms;
Y$^-$ is an anion such as bromide, chloride, acetate, borate, citrate, tartrate, bisulfate, bisulfite, sulfate or phosphate.

Preferably, the said amphoteric polymer comprises a repetition of only one unit of formula (IIa).

Among these units derived from a monomer of (meth)acrylamidoalkyltrialkylammonium type of formula (IIa), the ones that are preferred are those derived from the methacrylamidopropyltrimethylammonium chloride monomer, for which R$_3$ denotes a methyl radical, k is equal to 3, R$_5$, R$_6$ and R$_7$ denote a methyl radical, and Y$^-$ denotes a chloride anion.

Preferably, the units derived from a monomer of (meth)acrylic acid type (iii) are units of formula (IIIa):

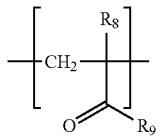

in which R$_8$ denotes H or CH$_3$ and R$_9$ denotes a hydroxyl radical or a —NH—C(CH$_3$)$_2$—CH$_2$—SO$_3$H radical.

The preferred units of formula (IIIa) correspond to the acrylic acid, methacrylic acid and 2-acrylamino-2-methyl-propanesulfonic acid monomers.

Preferably, the unit derived from a monomer of (meth)acrylic acid type of formula (IIIa) is that derived from acrylic acid, for which R$_8$ denotes a hydrogen atom and R$_9$ denotes a hydroxyl radical.

The acidic monomer(s) of (meth)acrylic acid type may be non-neutralized or partially or totally neutralized with an organic or mineral base.

Preferably, the said amphoteric polymer comprises a repetition of only one unit of formula (IIIa).

According to a preferred embodiment of the invention, the amphoteric polymer(s) of this type comprise at least 5 mol % of units derived from a monomer of (meth)acrylate or (meth)acrylamide type (i). Preferably, they comprise from 5 mol % to 30 mol % and more preferably from 10 mol % to 20 mol % of units derived from a monomer of (meth)acrylamide type.

The content of units derived from a monomer of (meth)acrylamidoalkyltrialkylammonium type (ii) may advantageously be from 10 mol % to 60 mol % and preferentially from 20 mol % to 55 mol %.

The content of units derived from an acidic monomer of (meth)acrylic acid type (iii) may advantageously be from 20 mol % to 70 mol % and preferentially from 30 mol % to 60 mol %.

According to a particularly preferred embodiment of the invention, the amphoteric polymer of this type comprises:
from 5 mol % to 30 mol % and more preferably from 10 mol % to 20 mol % of units derived from a monomer of (meth)acrylate or (meth)acrylamide type (i),
from 10 mol % to 60 mol % and preferentially from 20 mol % to 55 mol % of units derived from a monomer of (meth)acrylamidoalkyltrialkylammonium type (ii), and
from 20 mol % to 70 mol % and preferentially from 30 mol % to 60 mol % of units derived from a monomer of (meth)acrylic acid type (iii).

Amphoteric polymers of this type may also comprise additional units, other than the units derived from a monomer of (meth)acrylamide type, of (meth)acrylamidoalkyltrialkylammonium type and of (meth)acrylic acid type as described above.

However, according to a preferred embodiment of the invention, the said amphoteric polymers consist solely of units derived from monomers (i) of (meth)acrylate type, (ii) of (meth)acrylamidoalkyltrialkylammonium type and (iii) of (meth)acrylic acid type.

As examples of amphoteric polymers that are particularly preferred, mention may be made of methyl acrylate/methacrylamidopropyltrimethylammonium chloride/acrylic acid terpolymers. Such polymers are listed in the CTFA Dictionary (International Cosmetic Ingredient Dictionary) under the name Polyquaternium 47. Corresponding products are especially sold under the names Merquat® 2001 by the company Nalco.

As another type of amphoteric polymer that may be used, mention may also be made of copolymers based on (meth)acrylic acid and on a dialkyldiallylammonium salt, such as copolymers of (meth)acrylic acid and of dimethyldiallylammonium chloride. An example that may be mentioned is Merquat® 280 sold by the company Nalco.

According to a preferred embodiment, the polymer is present in the composition of the present invention, ranging from 0.01% to 3% by weight, preferably from 0.05% to 2% by weight, more preferably 0.1% to 1.5% by weight, relative to the total weight of the composition.

Fatty Acid Esters of Glycerol and of Polyglycerol

According to the invention, the composition comprises at least one fatty acid ester of glycerol and/or of polyglycerol.

According to a preferred embodiment, the fatty acid ester(s) of polyglycerol is (are) chosen from esters resulting from the reaction of polyglycerol comprising from 2 to 12 glycerol units, preferably from 3 to 10 glycerol units, and of at least one fatty acid containing from 8 to 24 carbon atoms, preferably from 8 to 22 carbon atoms, better still from 10 to 20 carbon atoms and even better still from 10 to 18 carbon atoms. The fatty acids containing from 8 to 24 carbon atoms may be linear or branched, and saturated or unsaturated.

The fatty acids may be chosen from oleic acid, stearic acid, isostearic acid, lauric acid, palmitic acid, myristic acid, linoleic acid, capric acid and caprylic acid, or mixtures thereof.

The fatty acid esters of polyglycerol can be chosen from monoesters, diesters, triesters and tetraesters, polyesters and mixtures thereof. Use is preferably made of esters with a low degree of esterification, for instance fatty acid monoesters, diesters or triesters of polyglycerol, or a mixture. The fatty acid ester of polyglycerol can be in the form of a mixture of esters with a low degree of esterification, for instance a mixture of monoester and diester or a mixture of monoester, diester and triester.

According to one embodiment, the fatty acid ester of polyglycerol is chosen from esters resulting from the reaction of polyglycerol comprising from 3 to 10 glycerol units and of at least one fatty acid containing from 8 to 20 carbon atoms, preferably from 10 to 18 carbon atoms, such as oleic acid or linoleic acid.

Mention may in particular be made of polyglyceryl-2 distearate, in particular as sold by NIHON EMULSION under the name Emalex PGSA; polyglyceryl-10 decastearate, in particular as sold by TAIYO KAGAKU under the name Sunsoft Q-1810S; glyceryl oleate, in particular as sold by COGNIS under the name Monomuls 90-O 18; glyceryl stearate, in particular as sold by COGNIS under the name Cutina GMS V; polyglyceryl-5 hexastearate, in particular as sold by TAIYO KAGAKU under the name Sunsoft A-186E; polyglyceryl-10 pentaoleate, in particular as sold by TAIYO KAGAKU under the name Sunsoft Q-175S; polyglyceryl-10 pentastearate, in particular as sold by TAIYO KAGAKU under the name Sunsoft Q-185S; glyceryl caprylate/caprate, in particular as sold by STEPAN under the name Stepan Mild GCC; polyglyceryl-10 heptaoleate, in particular as sold by TAIYO KAGAKU under the name Sunsoft Q-177S; polyglyceryl-4 isostearate, in particular as sold by EVONIK GOLDSCHMIDT under the name Isolan GI 34; diisostearoyl polyglyceryl-3 dimer dilinoleate, in particular as sold by EVONIK GOLDSCHMIDT under the name Isolan PDI; glyceryl laurate, in particular as sold by COGNIS under the name Monomuls 90-L 12; polyglyceryl-5 trioleate, in particular as sold by TAIYO KAGAKU under the name Sunsoft A-173E; polyglyceryl-2 oleate, in particular as sold by TAIYO KAGAKU under the name Sunsoft Q-17B; polyglyceryl-5 trimyristate, in particular as sold by TAIYO KAGAKU under the name Sunsoft A-143E; polyglyceryl-2 caprylate, in particular as sold by TAIYO KAGAKU under the name Sunsoft Q-81B; polyglyceryl-2 laurate, in particular as sold by TAIYO KAGAKU under the name Sunsoft Q-12D.

According to one particular embodiment, the fatty acid which is suitable for the reaction with the ester(s) of polyglycerol comprises at least one hydroxyl group. This is the case for ricinoleic acid. Mention may in particular be made of polyglyceryl-3 ricinoleate (and) sorbitan isostearate, in particular as sold by CRODA under the name Arlacel 1690, polyglyceryl-3 ricinoleate, in particular as sold by AARHUSKARLSHAMN under the name Akoline PGPR.

According to another embodiment, the fatty acid which is suitable for the reaction with the ester(s) of polyglycerol is a polyacid comprising at least one hydroxyl group.

For the purpose of the present invention, the fatty acid ester(s) are present in the composition ranging from 0.05% to 20% by weight, preferably from 0.1% to 10% by weight, relative to the total weight of the composition.

According to a preferred embodiment, the present invention relates to a composition comprising, in an aqueous phase, A) at least one anionic surfactant of $(C_6-C_{30})$alkyl sulfates;

B) at least one amphoteric or zwitterionic surfactant of $(C_8-C_{20})$alkylbetaines, $(C_8-C_{20}$ alkyl)amido$(C_2-C_8$ alkyl)betaines, or a mixture thereof;

C) at least one or alkyl(poly)glycoside nonionic surfactant is chosen from, alone or as a mixture, compounds of formula (I),

$$R_1O-(R_2O)_t-(G)_v \quad (I)$$

in which:

$R_1$ represents a linear or branched, saturated or unsaturated alkyl group containing from 8 to 18 carbon atoms, $R_2$ represents an alkylene group containing from 2 to 4 carbon atoms, G represents a glucose, fructose or galactose, preferably glucose, t denotes a value ranging from 0 to 4, and v denotes a value ranging from 1 to 4, D) at least one polymer chosen from cellulose ether derivatives comprising quaternary ammonium groups, polydiallyl dimethyl ammonium chlorides, methyl acrylate/methacrylamidopropyltrimethylammonium chloride/acrylic acid terpolymers, or a mixture thereof; and E) glyceryl oleate, According to another preferred embodiment, the composition of the present invention comprises, in an aqueous phase, relative to the total weight of the composition, a1) from 5% to 25% by weight of at least one anionic surfactant of $(C_6-C_{30})$alkyl sulfates;

b1) from 5% to 15% by weight of at least one amphoteric or zwitterionic surfactant of $(C_8-C_{20})$alkylbetaines, $(C_8-C_{20}$ alkyl)amido$(C_2-C_8$ alkyl)betaines, or a mixture thereof;

c1) from 0.1% to 3% by weight of at least one or alkyl(poly)glycoside nonionic surfactant is chosen from, alone or as a mixture, compounds of formula (I),

$$R_1O-(R_2O)_t-(G)_v \quad (I)$$

in which:

$R_1$ represents a linear or branched, saturated or unsaturated alkyl group containing from 8 to 18 carbon atoms, $R_2$ represents an alkylene group containing from 2 to 4 carbon atoms, G represents a glucose, fructose or galactose, preferably glucose, t denotes a value ranging from 0 to 4, and v denotes a value ranging from 1 to 4, d1) from 0.05% to 2% by weight of at least one polymer chosen from cellulose ether derivatives comprising quaternary ammonium groups, polydiallyl dimethyl ammonium chlorides, methyl acrylate/methacrylamidopropyltrimethylammonium chloride/acrylic acid terpolymers, or a mixture thereof; and e1) from 0.1% to 10% by weight of glyceryl oleate, The composition according to the present invention may further comprise one or more plant oils and/or mineral oils, as conditioning agent.

The term "oil" means any nonionic lipophilic compound that is insoluble in water and liquid at room temperature (25° C.) and at atmospheric pressure. For the purposes of the present invention, the term "water-insoluble" refers to a compound whose solubility at spontaneous pH in water at 25° C. and at atmospheric pressure is less than 1% and preferably less than 0.5%. The oils preferably have a melting point of less than 5° C. and a viscosity of less than 500 cPs at 25° C. at a shear rate of 1 s-1.

In particular, the term "plant oil" means a cosmetically acceptable oil as defined above, obtained from a species belonging to the plant kingdom.

The term "mineral oils" means hydrocarbons in the form of linear or branched, saturated or unsaturated oils, of mineral or synthetic origin, and which may be hydrogenated.

Preferably, mineral oils are used in the present invention.

The mineral oils used in the present invention are chosen from the mineral oils as defined above, usually used in the cosmetics field.

As examples of mineral oils that may be used in the present invention, mention may be made of:

mixtures of hydrocarbon-based oils derived from petroleum (INCI name: Mineral Oil), volatile or non-volatile liquid paraffin, liquid petroleum jelly, polyolefins and in particular polydecenes, isoparaffins such as isohexadecane, isododecane and hydrogenated polyisobutylenes such as Parleam® oil sold by the company NOF Corporation (INCI name: Hydrogenated polyisobutene).

Among the mineral oils mentioned above, the following are preferably used:

mixtures of hydrocarbon-based oils derived from petroleum, volatile or non-volatile liquid paraffin, and liquid petroleum jelly, and polyolefins and in particular polydecenes.

The term "polydecenes" means any compound of formula $C_{10n}H_{(20n)+2}$ in which n ranges from 3 to 9, corresponding to the name "polydecene" in the CTFA dictionary, 7th edition, 1997 of the Cosmetic, Toiletry and Fragrance Association, USA, and also to the same INCI name in the USA and in Europe. These are poly-1-decene hydrogenation products. Among these compounds, those for which, in the formula, n ranges from 3 to 7 are more particularly chosen according to the invention.

Examples that may be mentioned include the products sold under the name Silkflo® 366 NF Polydecene by the company Amoco Chemical, and those sold under the names Nexbase® 2002 FG, 2004 FG, 2006 FG and 2008 FG by the company Fortum.

The preferred mineral oil is mixtures of hydrocarbon-based oils derived from petroleum (INCI name: Mineral Oil), volatile or non-volatile liquid paraffin, or a mixture thereof.

Mentions may be made of the product (INCI name: mineral oil) sold under the tradename Emcaplus 70 by the company Oxiteno.

The total amount of oil(s), when they are present in the composition, preferably ranges from 0.01% to 20% by weight, better still from 0.05% to 10% by weight and more particularly from 0.1% to 5% by weight relative to the total weight of the final composition.

The compositions according to the invention may naturally contain, in addition, all the standard adjuvants encountered in the field of shampoos, such as, for example, perfumes, preservatives, sequestering agents, thickeners, hydrating agents, anti-dandruff or antiseborrhoeic agents, vitamins, sunscreen agents, suspending agents and the like.

The composition according to the invention may take the form of liquid, creams or gel.

Another aspect of the invention is a process for washing and/or conditioning keratin fibers, especially the hair, comprising the steps of applying to said fibers the composition of the invention, and then rinsing with water after an optional period of exposure.

Yet another aspect of the present invention is the use of the above composition of the invention for washing and/or conditioning keratin fibers, especially hair.

Non limiting examples illustrating the invention are given.

EXAMPLES

Three hair shampoos were prepared, one according to the invention (Invention A) and two comparative (Comparative B and C):

| Ingredient | Invention (% active by weight) | | | | Comparative (% active by weight) | | |
| --- | --- | --- | --- | --- | --- | --- | --- |
| | A | B | C | D | A | B | C |
| SODIUM LAURETH SULFATE (2EO) (Texapon ® AOS 225 UP from Cognis (BASF)) | 10.00 | 10.00 | 10.00 | 10.00 | 10.00 | 10.00 | 10.00 |
| COCAMIDOPROPYL BETAINE (Dehyton ® PK 45 from Cognis (BASF)) | 7.00 | 7.00 | 7.00 | 7.00 | 7.00 | 7.00 | 7.00 |
| POLYQUATERNIUM-10 (UCARE polymer JR 30M from DOW) | 0.20 | 0.20 | 0 | 0 | 0 | 0.20 | 0.20 |
| POLYQUATERNIUM-6 (Merquat ® 100from Nalco) | 0 | 0 | 0.20 | 0 | 0 | 0 | 0 |

-continued

| Ingredient | Invention (% active by weight) | | | | Comparative (% active by weight) | | |
|---|---|---|---|---|---|---|---|
| | A | B | C | D | A | B | C |
| POLYQUATERNIUM-47 (Merquat ® 2001 from Nalco) | 0 | 0 | 0 | 0.20 | 0 | 0 | 0 |
| Guar hydroxypropyl trimonium chloride | 0 | 0 | 0 | 0 | 0.20 | 0 | 0 |
| Glyceryl oleate (Monomuls 90-O from Cognis (BASF)) | 0.40 | 0.40 | 0.40 | 0.40 | 0.40 | 0 | 0.40 |
| Decyl glucoside (53%, Plantacare ® 2000UP from Cognis (BASF)) | 0.60 | 0.60 | 0.60 | 0.60 | 0.60 | 0.60 | 0 |
| Mineral oil (Paraffinum liquidum emcaplus from Oxiteno) | 0 | 0.20 | 0 | 0 | 0 | 0.20 | 0.20 |
| SALICYLIC ACID | 0.20 | 0.20 | 0.20 | 0.20 | 0.20 | 0.20 | 0.20 |
| SODIUM BENZOATE | 0.50 | 0.50 | 0.50 | 0.50 | 0.50 | 0.50 | 0.50 |
| Glycerin | 2.00 | 2.00 | 2.00 | 2.00 | 2.00 | 2.00 | 2.00 |
| WATER | Qs to 100 | Qs to 100 | Qs to 100 | Qs to 100 | Qs to 100 | Qs to 100 | Qs to 100 |
| pH | 5.5 | 5.5 | 5.5 | 5.5 | 5.5 | 5.5 | 5.5 |

Comparative A used a polymer which is not in the scope of the invention; Comparative B did not contain glycerol oleate; Comparative C did not contain decyl glucoside.

The invention A to D, comparative A to C were prepared according to the conventional methods for preparing shampoo formulations.

Transparency

The transparency was evaluated by the turbidity, using a 2100N Turbidimeter machine from HACH.

The term "transparent or translucent" is understood to mean a composition having a turbidity of less than 400 NTU (Nephelometric Turbidity Units) at 25° C. and preferably of less than 250 NTU at 25° C.

| Attributes | Invention | | | | Comparative | | |
|---|---|---|---|---|---|---|---|
| | A | B | C | D | A | B | C |
| Reduction of dry combing force (Natural black Chinese hair) | 13.57% | 22.82% | 12.15% | 14.83% | 6.27% | 18.33% | 20.02% |
| Turbidity (NTU) | 40 | 36.7 | 33.6 | 54.7 | 1300 | 2229 | 2402 |

The reduction of the dry combing force on the natural hair of the Invention A to D, and Comparative A to C were measured.

Dry Combing after Rinsing 0.4 g of the examples of Invention A and Comparative B, C samples were applied on 6 g, 25 cm length of natural black Chinese hair, respectively. The hair was washed then the samples were left on the hair for 10 minutes. Then the hair was rinsed by warm water for 15 seconds, and left to dry over night at room temperature. After 5 times repeated application using the process described herein, the combing force between the hair stress and a comb was measured by the device named Combing Tester JC45A-001, sold by JAU CHUNG. The reduction of combing force was measured based on the following formula:

Reduction of combing force (%)=[combing force of control(9% of sodium laureth sulfate)−combing force of example)/combing force of 9% sodium laureth sulfate]×100%.

It is considered that, when the reduction of combing force is greater than or equal to 10%, the product possesses an acceptable effect on reduction of combing force. The higher the number, the better effect is present.

The transparencies of the Invention A to D, and the Comparative A to C mentioned above were evaluated.

Inventions A to D possess very good effect on reduction of combing force on natural hair, whereas Comparative A is not acceptable.

In terms of appearance, all the Inventions A to D are pleasantly transparent, whereas Comparative A to C are not transparent.

In conclusion, the invention has an improved reduction on combing force of natural hair, and moreover a pleasant transparent appearance.

What is claimed is:

1. A shampoo composition comprising, in an aqueous phase:
   a) from 0.1% to 50% by weight of sodium laureth sulfate (2EO)
   b) from 5% to 15% by weight of Cocamidopropyl betaine
   c) from 0.1% to 3% by weight of decyl glucoside
   d) from 0.01% to 3% by weight of Polyquaternium-10
   e) from 0.05% to 20% by weight of glycerol oleate
   wherein the % by weights are relative to the total weight of the composition; and
   wherein the composition is transparent and free of silicone.

2. The shampoo composition of claim 1, further comprising at least one oil, in an amount ranging from 0.01% to 20% by weight, relative to the total weight of the composition.

3. A process for washing and conditioning hair, comprising:
applying the composition of claim 1 to said hair; and then rinsing with water.

* * * * *

UNITED STATES PATENT AND TRADEMARK OFFICE
CERTIFICATE OF CORRECTION

PATENT NO. : 10,993,901 B2  
APPLICATION NO. : 15/531025  
DATED : May 4, 2021  
INVENTOR(S) : Jia et al.

Page 1 of 1

It is certified that error appears in the above-identified patent and that said Letters Patent is hereby corrected as shown below:

On the Title Page

Item [56], Line 4, delete "Schwarzkoph" and insert -- Schwarzkopf --, therefor.

Signed and Sealed this  
Thirtieth Day of November, 2021

Drew Hirshfeld  
*Performing the Functions and Duties of the*  
*Under Secretary of Commerce for Intellectual Property and*  
*Director of the United States Patent and Trademark Office*